(12) United States Patent
Shechter

(10) Patent No.: US 7,902,816 B2
(45) Date of Patent: Mar. 8, 2011

(54) ELECTROMAGNETIC TRACKING METHOD AND APPARATUS FOR COMPENSATION OF METAL ARTIFACTS USING MODULAR ARRAYS OF REFERENCE SENSORS

(75) Inventor: Guy Shechter, Briarcliff Manor, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 444 days.

(21) Appl. No.: 12/095,742

(22) PCT Filed: Dec. 11, 2006

(86) PCT No.: PCT/IB2006/054748
§ 371 (c)(1),
(2), (4) Date: Jun. 2, 2008

(87) PCT Pub. No.: WO2007/069186
PCT Pub. Date: Jun. 21, 2007

(65) Prior Publication Data
US 2008/0309326 A1    Dec. 18, 2008

Related U.S. Application Data

(60) Provisional application No. 60/750,756, filed on Dec. 15, 2005.

(51) Int. Cl.
*G01B 7/00* (2006.01)
*G01B 7/14* (2006.01)
(52) U.S. Cl. .............. 324/207.12; 324/200; 324/207.17; 324/207.23
(58) Field of Classification Search .......... None
See application file for complete search history.

(56) References Cited

U.S. PATENT DOCUMENTS

| 5,831,260 | A | 11/1998 | Hansen |
| 6,161,032 | A * | 12/2000 | Acker ........................ 600/424 |
| 6,377,041 | B1 | 4/2002 | Jones, Jr. et al. |
| 6,400,139 | B1 | 6/2002 | Khalfin et al. |
| 7,782,046 | B2 * | 8/2010 | Anderson ............... 324/207.17 |
| 2008/0238413 | A1 * | 10/2008 | Anderson ............... 324/207.17 |
| 2009/0001969 | A1 * | 1/2009 | Berkcan .................. 324/207.16 |

FOREIGN PATENT DOCUMENTS

| GB | 2331807 A | 6/1999 |
| WO | WO0133231 A2 | 5/2001 |

* cited by examiner

*Primary Examiner* — Vinh P Nguyen

(57) ABSTRACT

An electromagnetic tracking method includes generating an electromagnetic field (14) in a region of interest (16). The electromagnetic field is subject to distortion in response to a presence of metal artifacts proximate the electromagnetic field. An array of reference sensors (30,50,102,104,110) having a predefined known configuration are disposed proximate the region of interest. A first set of locations of the array of reference sensors is determined with respect to the electromagnetic field generator (12) in response to an excitation of one or more of the reference sensors via the electromagnetic field. A second mechanism (28), other than the electromagnetic field, determines a first portion of a second set of locations of at least one or more sensors of the array of reference sensors with respect to the second mechanism, the second mechanism being in a known spatial relationship with the electromagnetic field generator. A remainder portion of the second set of locations of the reference sensors of the array of reference sensors is determined in response to (i) the first portion of the second set of locations determined using the second mechanism and (ii) the predefined known configuration of the array of reference sensors. The method further includes compensating for metal distortion of the electromagnetic field in the region of interest as a function of the first and second sets of reference sensor locations of the array of reference sensors.

26 Claims, 7 Drawing Sheets

ELECTROMAGNETIC TRACKING METHOD AND APPARATUS FOR COMPENSATION OF METAL ARTIFACTS USING MODULAR ARRAYS OF REFERENCE SENSORS

CROSS REFERENCE TO RELATED APPLICATIONS

This application claims the benefit of International Application Number PCT/IB2006/054748, filed Dec. 11, 2006, and U.S. Provisional Application Ser. No. 60/750,756 filed Dec. 15, 2005 which are incorporated herein in whole by reference.

The present embodiments relate generally to electromagnetic tracking methods and apparatus and more particularly, to an electromagnetic tracking method and apparatus for compensation of metal artifacts using modular arrays of reference sensors.

Image guidance is routinely used to improve outcomes of minimally invasive medical procedures. Imaging provides the physician a view into the patient's anatomy. The position of needles and catheters can be shown with relation to the anatomic or functional images to help the physician target his treatment more quickly and accurately.

Electromagnetic tracking systems (EMTS) are used to localize objects by establishing a small magnetic field around the site of the intervention. EMTS technology is suited for non-line-of-sight applications such as the insertion of a biopsy needle, through the skin, into a liver tumor. In particular, percutaneous liver biopsies require that a needle be inserted through the skin and targeted to the location of a tumor. The physician can use CT data as an anatomical roadmap to guide the procedure. During the procedure, the position of a biopsy needle could be superimposed on the images to help the physician steer toward the tumor.

Since the tip of the needle is not visible when it is embedded in the abdomen, electromagnetic tracking systems (EMTS) are used to track the position of the needle. A simple EMTS consists of a field generator and a sensor coil. The coil is placed at the tip of a needle, where it measures a magnetic field produced by the field generator. This measurement provides the spatial location of the needle relative to the field generator.

Unfortunately, metal objects distort the EMTS field, thereby limiting the accuracy of the sensor's position and orientation measurements. Metal artifacts might arise from the patient table, imaging system, or medical instruments. In particular, ferromagnetic and conductive metal objects distort the magnetic field generated by the EMTS field generator. The distortion affects the measurements made by the sensor coils, thereby limiting the accuracy of a sensor's position and orientation measurements.

Accordingly, an improved method and system for overcoming the problems in the art is desired.

In the figures, like reference numerals refer to like elements. In addition, it is to be noted that the figures may not be drawn to scale.

Figure 1:
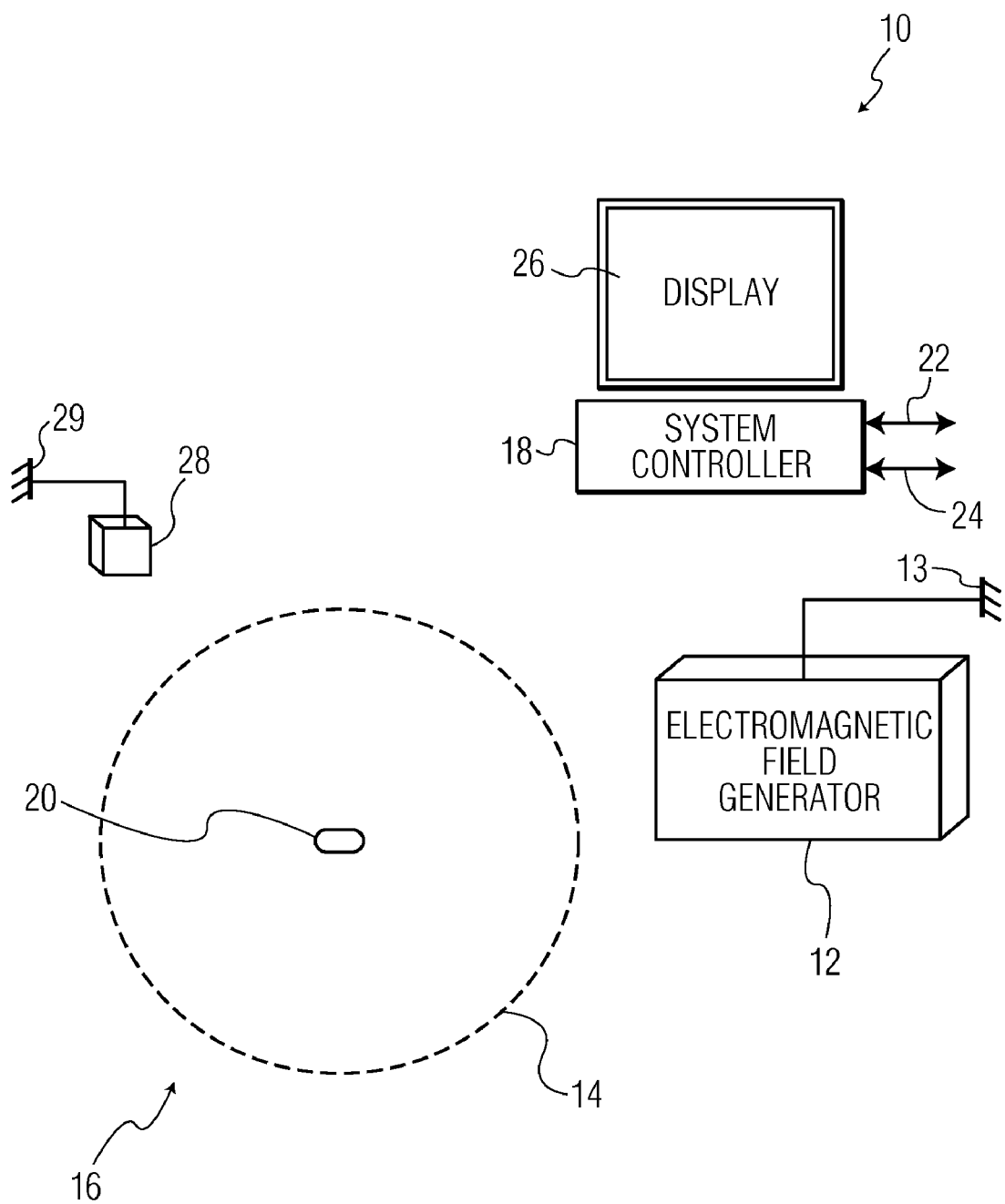
FIG. 1 is a block diagram view of an electromagnetic tracking system according to an embodiment of the present disclosure.

FIG. 1 is a block diagram view of an electromagnetic tracking system 10 featuring compensation of metal artifacts according to an embodiment of the present disclosure. An electromagnetic field generator 12 generates an electromagnetic field 14 in a region of interest, generally indicated by reference numeral 16. Electromagnetic field generator 12 is referenced to a fixed location, as indicated by reference number 13. The electromagnetic field 14 is subject to distortion in response to a presence of metal artifacts (not shown) proximate the electromagnetic field and the region of interest. A system controller 18 is configured for determining a location of a sensor 20 to be tracked (the sensor being located within the region of interest 16) as a function of the metal distortion compensated electromagnetic field, as to be discussed further herein.

System controller 18 can comprise any suitable computer and/or sensor interfaces, the controller further being programmed with suitable instructions for carrying out the various functions as discussed herein with respect to performing metal distortion compensation for electromagnetic field tracking. System controller 18 may include various input/output signal lines, such as 22 and 24, for example, for being electronically coupling to other elements of the electromagnetic tracking system 10. A suitable display device 26 is coupled to system controller 18, for example, for use by a system operator during a given electromagnetic tracking application. Furthermore, additional devices, such as input/output devices, pointing devices, etc. (not shown) may be provided, as may be necessary, for a given implementation of electromagnetic tracking application.

Electromagnetic tracking system 10 further includes a second tracking mechanism 28. The second tracking mechanism 28 is referenced to a fixed location, as indicated by reference number 29. In one embodiment, the input/outputs 22 and 24 of system controller 18 could be coupled to electromagnetic field generator 12 and to the second tracking mechanism 28, respectively. The second mechanism 28 is configured for determining the spatial relationship between the second mechanism 28 and the electromagnetic field generator 12. In one embodiment, the second mechanism 28 comprises an optical tracking system suitable for providing a desired distance and location information for a given electromagnetic tracking application, as discussed herein.

In one embodiment, the array of reference sensors comprises one or more modular arrays, each modular array having (i) a predefined configuration or shape and (ii) one or more reference sensors. For example, the modular array can comprise an array having a semi-cylindrical shape, the semi-cylindrical shaped array being configured for use with interventions conducted around one or more of the abdomen or thorax of a patient. In another example, the modular array can comprise a substantially flat panel array, the flat panel array including one or more reference sensors in a predefined configuration, the flat panel array further being configured for placement underneath a patient. In yet another example, the modular array can comprise an array having a cage shape, the cage array being configured for interventions in a peripheral limb of a patient.

Figure 2:
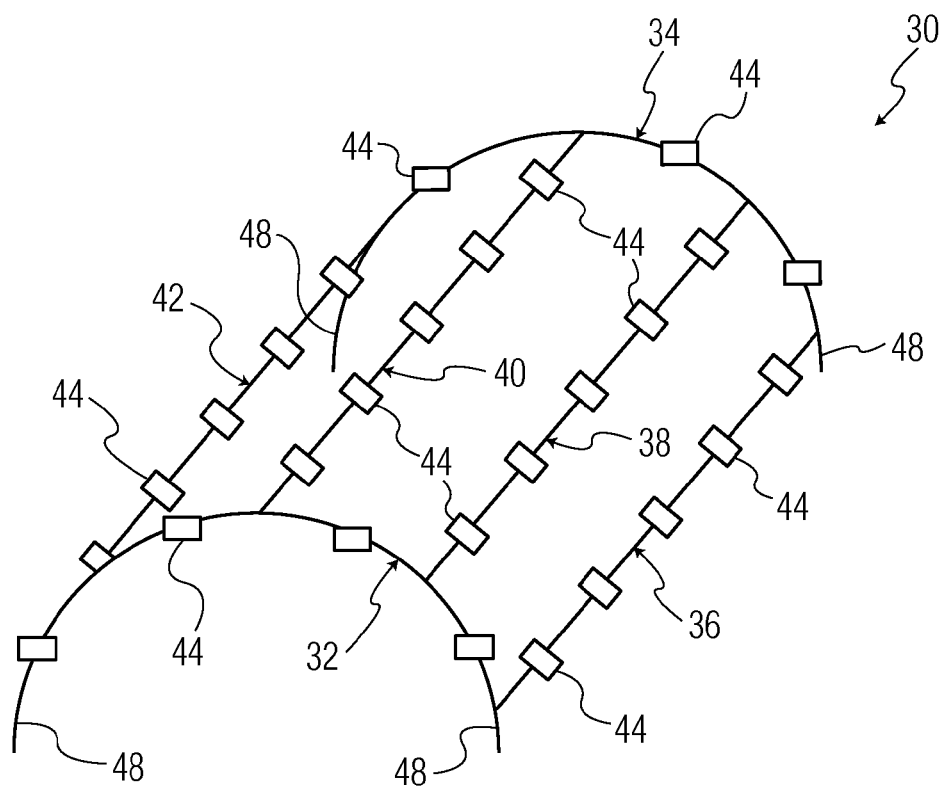
FIG. 2 is a schematic diagram view illustrating an array of reference sensors in one configuration of the electromagnetic tracking system and method according to an embodiment of the present disclosure.

FIG. 2 is a schematic diagram view illustrating an array of reference sensors in one configuration 30 according to an embodiment of the present disclosure. The array of reference sensors 30 can be embedded within a non-metallic material of a desired shape. The non-metallic material can comprise, for example, any suitable plastic having characteristics appropriate for maintaining the desired shape. The desired shape can include, for example, a semi-cylindrical shape as shown in FIG. 2. In the embodiment of FIG. 2, the array of reference sensors 30 can comprise one or more modular arrays 32, 34, 36, 38, 40, 42, etc., each modular array having (i) a predefined configuration or shape and (ii) one or more reference sensors 44.

The array of reference sensors 30 can thus be characterized by a given overall number of reference sensors in a given overall configuration. Accordingly, with knowledge of the positioning of at least two of the sensors within the overall configuration, the position and location information for a remainder of the sensors can be determined as a function of predetermined configuration information of the array of reference sensors.

Figure 3:
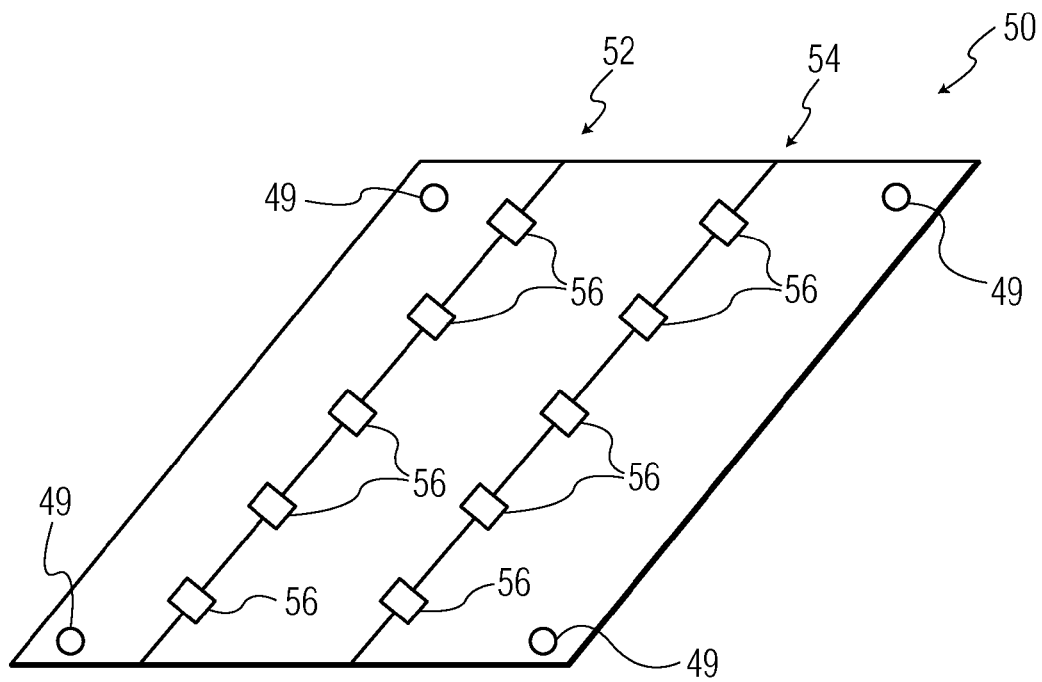
FIG. 3 is a schematic diagram view illustrating an array of reference sensors in another configuration of the electromagnetic tracking system and method according to another embodiment of the present disclosure.

FIG. 3 is a schematic diagram view illustrating an array of reference sensors in another configuration 50 according to another embodiment of the present disclosure. The array of reference sensors can be embedded within a non-metallic material of a desired shape. The non-metallic material can comprise, for example, any suitable plastic having characteristics appropriate for maintaining the desired shape. The desired shape can include, for example, a substantially flat panel shape as shown in FIG. 3. In the embodiment of FIG. 3, the array of reference sensors 50 can comprise one or more modular arrays 52, 54, etc., each modular array having (i) a predefined configuration or shape and (ii) one or more reference sensors 56.

Accordingly, the array of reference sensors 50 can thus be characterized by a given overall number of reference sensors in a given overall configuration. Accordingly, with knowledge of the positioning of at least two or more of the sensors within the overall configuration, the position and location information for a remainder of the sensors can be determined as a function of predetermined configuration information of the array of reference sensors.

The modular array can further comprise one or more modular portions of prefabricated sensor arrays. In such an embodiment, the modular portions can further include at least two registration mechanisms, generally indicated by reference numerals 48 and 49, of FIGS. 2 and 3, respectively. The registration mechanisms are for use in establishing a predefined placement of the modular portions together. Furthermore, the at least two registration mechanisms comprise interlocking mechanisms. The interlocking mechanisms are for use in locking two or more modular arrays together in a predefined arrangement. As a result of locking the two or more modular arrays together, the interlocking mechanisms ensure the ability to perform a registration of a location of the array of reference sensors with respect to a positioning of the electromagnetic field generator.

In one embodiment, the flat panel can comprise a piece of plastic having a length dimension that spans an average patient's thorax and abdomen and a width dimension commensurate with a width of a CT or X-ray table. The thickness of the flat panel can be on the order of approximately one centimeter (1 cm). The flat panel is prepared with sockets drilled into the plastic, the sockets being suitable for accommodating sensors for use with the electromagnetic tracking system. In one embodiment, sockets are arranged in a grid formation with a nominal horizontal and vertical spacing on the order of one inch. In a similar manner, the semi-cylindrical array of reference sensors 30 can be fabricated with embedded reference sensors. The semi-cylindrical array 30 can further be provided with molded pegs and the flat panel 50 with holes in the plastic, so that the two pieces of plastic can be fixed temporarily with respect to each other, e.g., around a patient.

Figure 4:
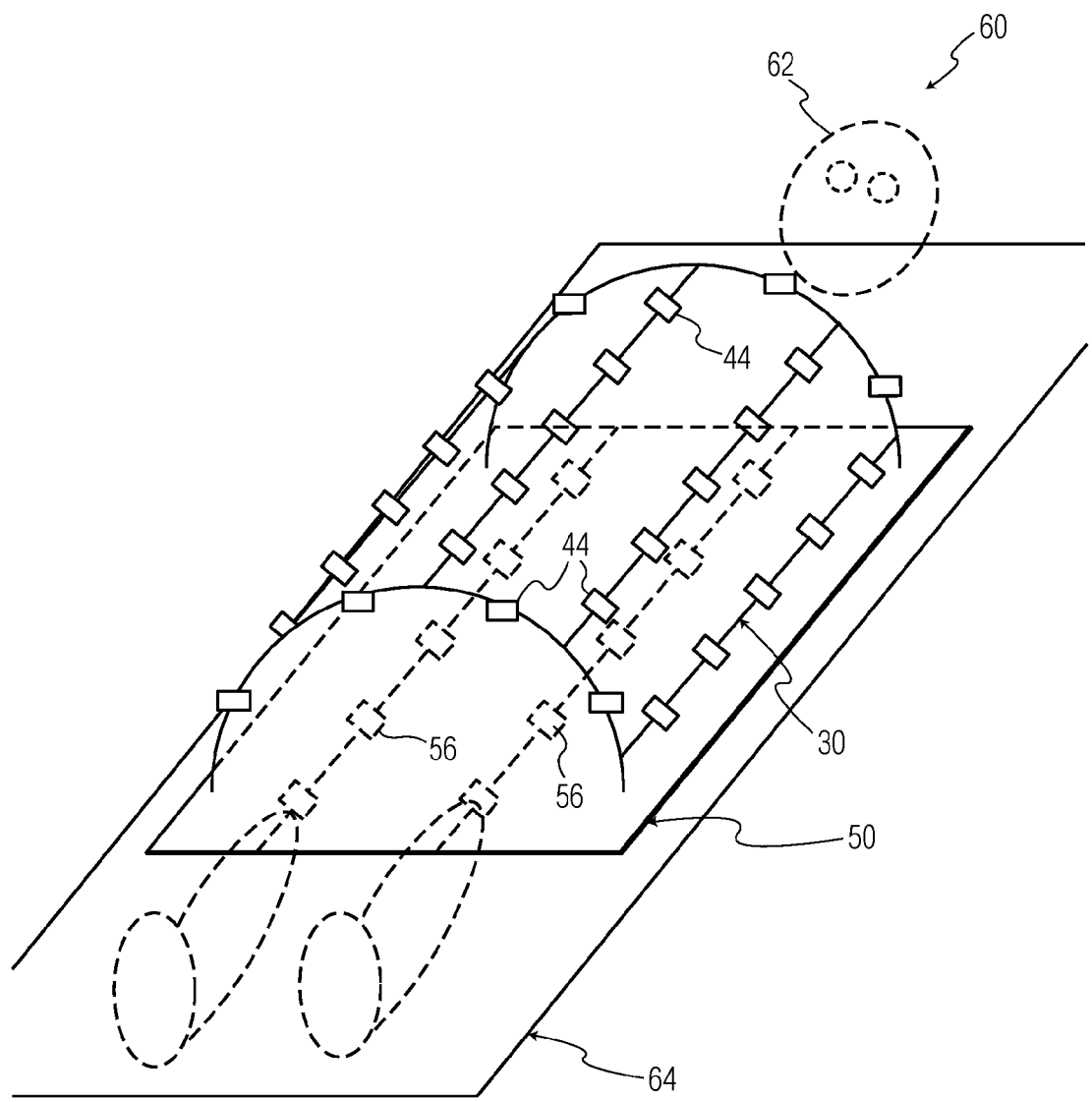
FIG. 4 is a schematic diagram view illustrating multiple arrays of reference sensors of different configurations joined together according to an embodiment of the present disclosure.

FIG. 4 is a schematic diagram view illustrating multiple arrays of reference sensors of different configurations joined together, generally indicated by reference numeral 60, according to an embodiment of the present disclosure. The array of reference sensors as illustrated in FIG. 4 thus comprises first and second reference sensor arrays, 30 and 50, respectively. The first reference sensor array 30 includes a first configuration of one or more reference sensors 44 and the second reference sensor array 50 includes a second configuration of one or more reference sensors 56. In addition, the configuration of the first reference sensor array 30 can be different from the configuration of the second reference sensor array 50.

As illustrated in FIG. 4, one embodiment of the present disclosure is applicable for a liver biopsy. The flat panel array 50 is configured for placement underneath a patient's back, the patient generally indicated in phantom lines by reference numeral 62. The other array 30, comprising a semi-cylindrical array is configured for placement around the patient's abdomen. In addition, the flat panel array 50 is intended for use on a table 64 containing metal components, wherein the table 64 can comprise one or more of an X-ray table or a CT table.

Figure 5:
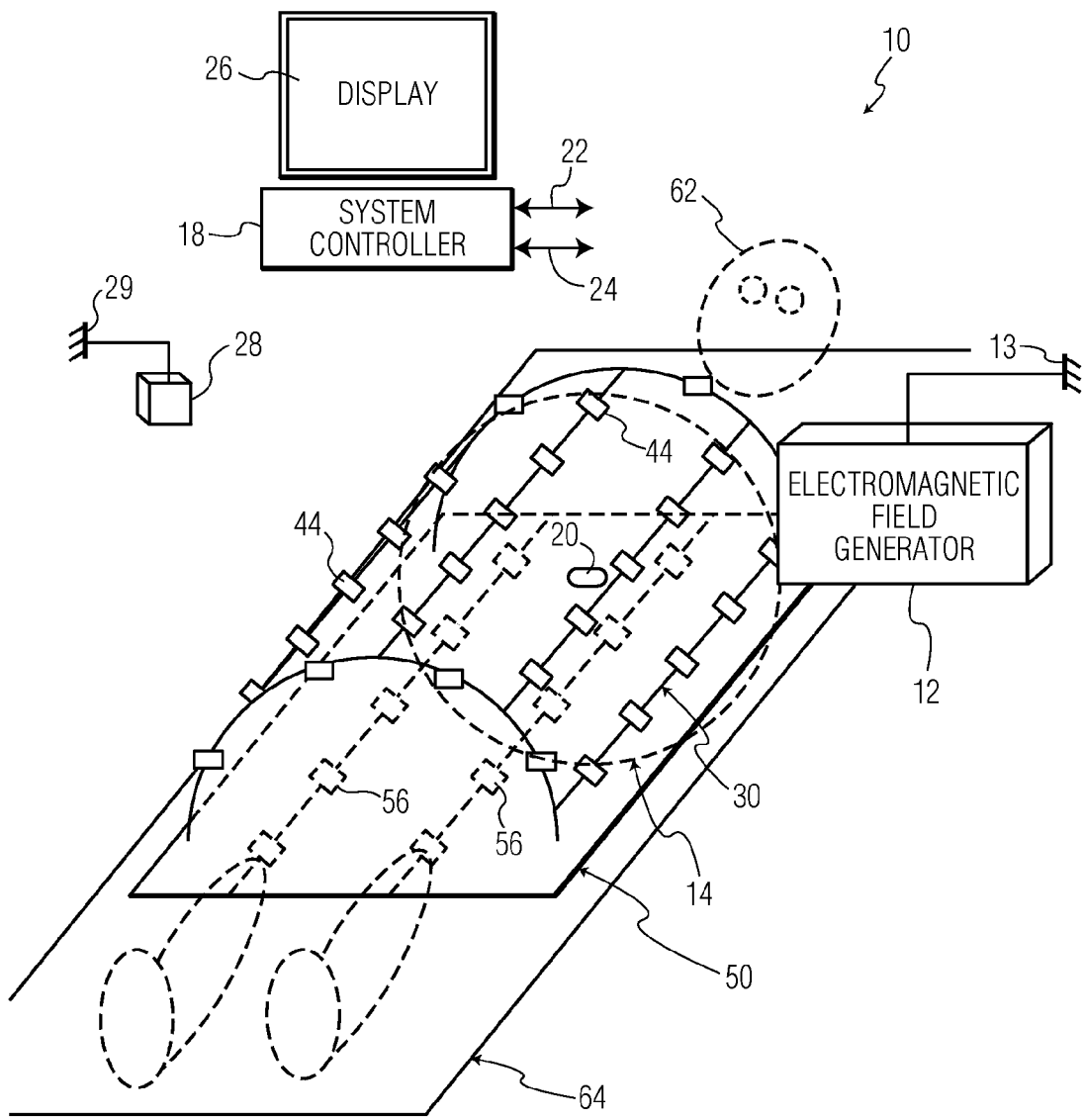
FIG. 5 is a block diagram view of an electromagnetic tracking system including multiple arrays of reference sensors of different configurations joined together according to an embodiment of the present disclosure.

FIG. 5 is a block diagram view of an electromagnetic tracking system 10 including multiple arrays of reference sensors of different configurations (30,50) joined together according to an embodiment of the present disclosure. At least one array of reference sensors (30,50) is disposed proximate the region of interest, the at least one array of reference sensors having a predefined known configuration. In this embodiment, the system controller 18 is configured for determining a first set of locations of the array of reference sensors (30,50) with respect to the electromagnetic field generator 12 in response to an excitation of one or more of the reference sensors (44,56) via the electromagnetic field 14. The second mechanism 28, other than the electromagnetic field generator 12, determines a first portion of a second set of locations of at least one or more sensors of the array of reference sensors (30,50) with respect to the second mechanism 28. The one or more sensors are configured for providing a description of the three dimensional (3D) orientation and position of the modular array of reference sensors. In addition, the second mechanism 28 is in a known spatial relationship with the electromagnetic field generator 12. The system controller (18) determines a remainder portion of the second set of locations of the reference sensors (44,56) of the array of reference sensors (30,50) in response to (i) the first portion of the second set of locations determined using the second mechanism (28) and (ii) the predefined known configuration of the array of reference sensors (30,50). Furthermore, the system controller 18 is configured for performing compensation for metal distortion of the electromagnetic field in the region of interest as a function of the first and second sets of reference sensor locations of the array of reference sensors.

For a CT guided liver biopsy, the flat rectangular array 50 is placed on top of the CT table 64. The patient 62 would be positioned on top of the rectangular array 50. Then the semi-cylindrical array 30 would be placed on top of the patient, and securely locked into the flat panel array 50. Next, the location of the reference arrays (30,50) are registered to the position of the field generator 12. In one embodiment, the localization is performed with an optical tracker 28 that can see both the reference sensor arrays (30,50) and the field generator 12. During the procedure, the system controller acquires position measurements from the reference sensors (30,50). The true positions of the sensors would be computed using: (1.) knowledge of the relative position of the sensors within each array, which is determined during the fabrication process; and (2.) knowledge of the relative position of each array to the field generator, which is determined in this embodiment using the optical tracker. These measurements would then be used to quantify and correct distortions of the electromagnetic field, for example, using algorithms as disclosed in U.S. Pat. Nos. 6,400,139 and 6,377,041.

Figure 6:
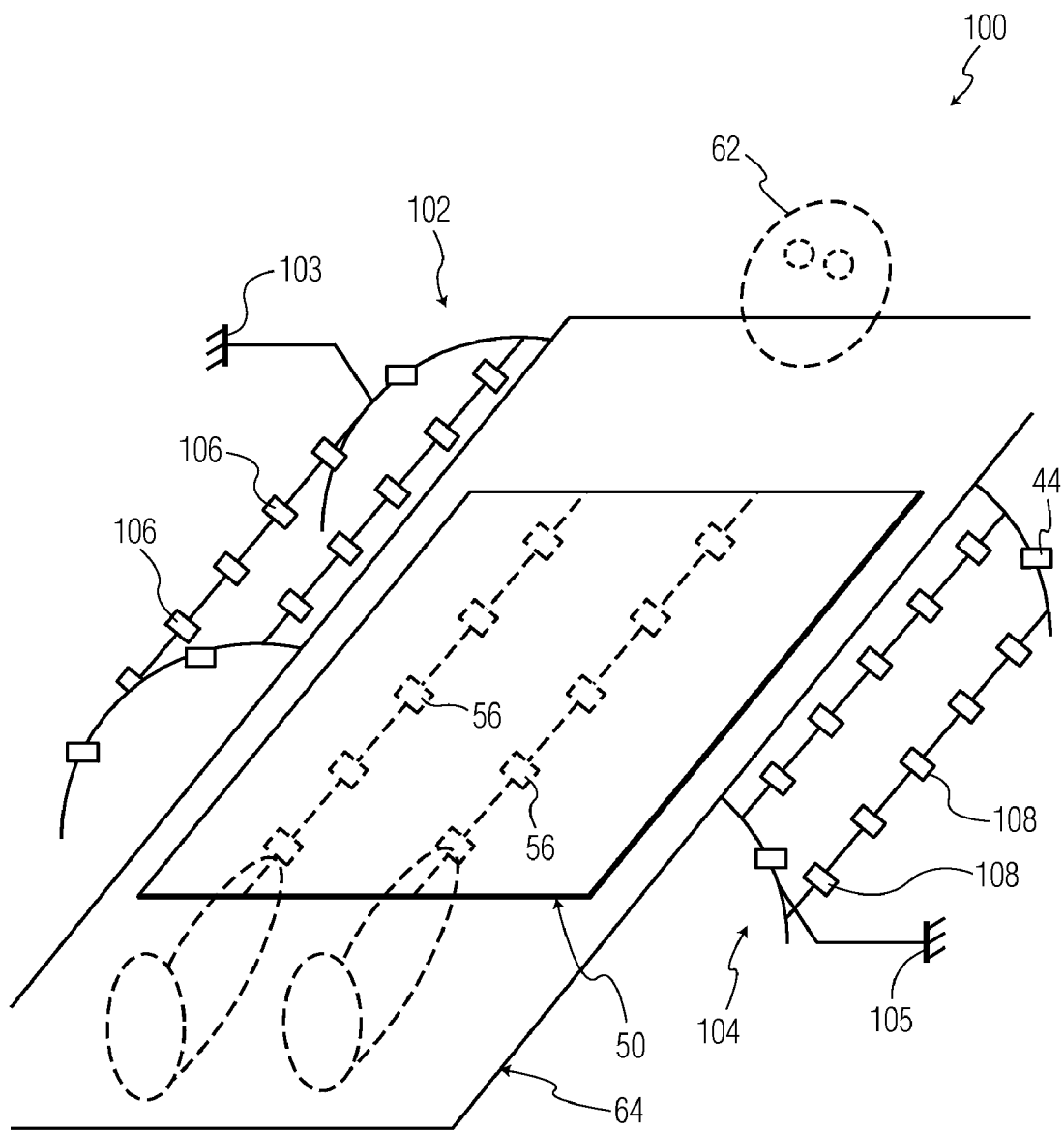
FIG. 6 is a schematic diagram view illustrating multiple arrays of reference sensors of different configurations physically spaced apart from one another according to another embodiment of the present disclosure.
Figure 7:
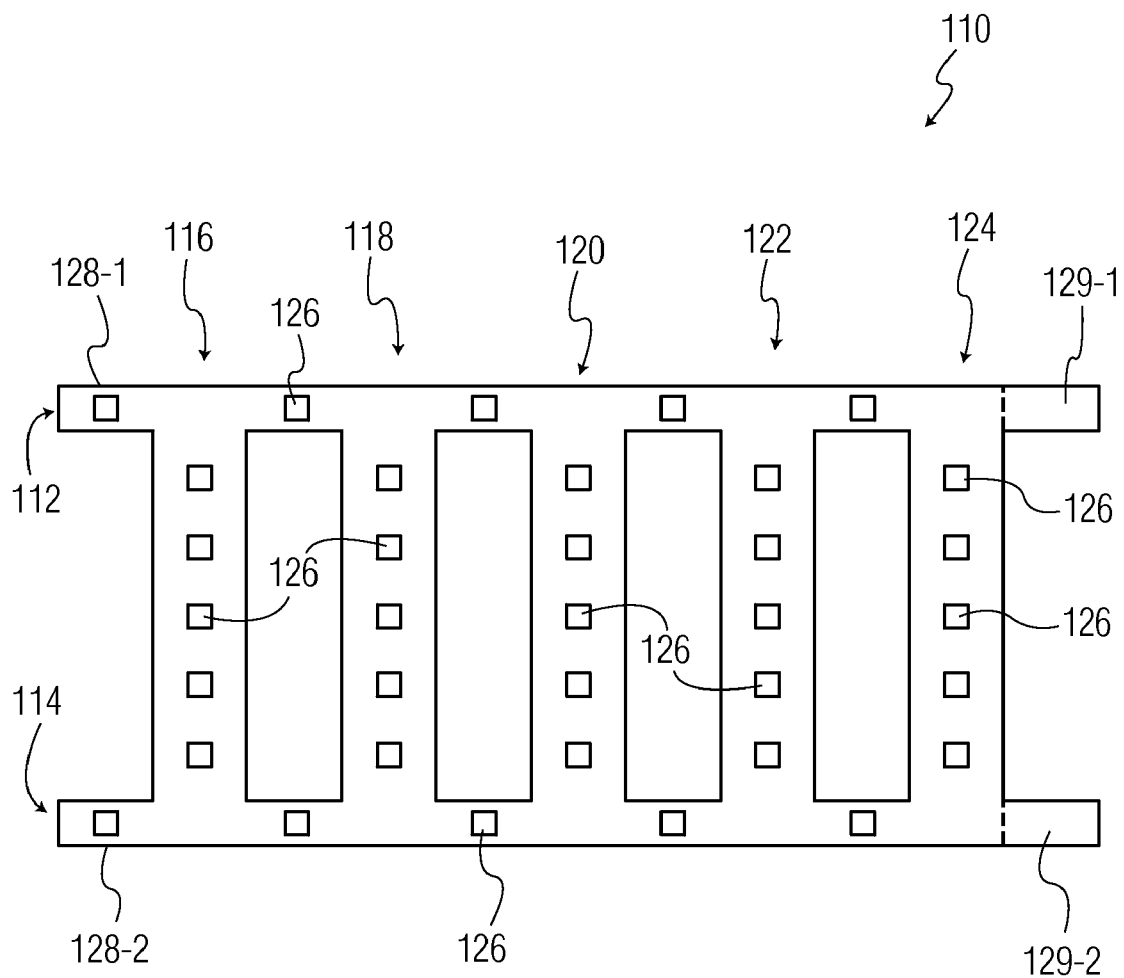
FIG. 7 is a schematic diagram view illustrating an array of reference sensors in yet another configuration according to another embodiment of the present disclosure.

FIG. 6 is a schematic diagram view of an electromagnetic tracking system implementation 100 illustrating multiple arrays of reference sensors of different configurations (50, 102,104) physically spaced apart from one another according to another embodiment of the present disclosure. In this embodiment, the array of reference sensors (50,102,104) each comprises multiple arrays of reference sensors (56,106, 108). For example, a first array of reference sensors is generally indicated by reference numeral 50. A second array of reference sensors is generally indicated by reference numeral 102. The second array of reference sensors 102 is referenced to a fixed location, as indicated by reference number 103. A third array of reference sensors is generally indicated by reference numeral 104. The third array of reference sensors 104 is referenced to a fixed location, as indicated by reference number 105. In this embodiment, the second array of reference sensors 102 can be maintained physically separate from the first array of reference sensors 50. The second array of reference sensors 102 can also be maintained physically separate from the third array of reference sensors 104, and so on. FIG. 7 is a schematic diagram view illustrating an array of reference sensors 110 in yet another configuration according to another embodiment of the present disclosure. The array of reference sensors 110 is embedded within a non-metallic material of a desired shape. The non-metallic material can comprise, for example, any suitable plastic having characteristics appropriate for maintaining the desired shape. The desired shape can include, for example, a cage shape. The shape as shown in FIG. 7 illustrates a fairly planar shape of the array of reference sensors prior to being formed into the desired cage shape of FIG. 8. In the embodiment of FIG. 7, the array of reference sensors 110 can comprise one or more modular arrays 112, 114, 116, 118, 120, 122, 124 etc., each modular array having (i) a predefined configuration or shape and (ii) one or more reference sensors 126.

The modular array of FIG. 7 can further include at least two registration mechanisms, generally indicated by reference numerals (128-1, 128-2) and (129-1, 129-2). The registration mechanisms are for use in establishing a predefined placement of the modular portions together. Furthermore, the at least two registration mechanisms can comprise any suitable interlocking mechanisms. For example, the interlocking mechanisms may include complementary interlocking tabs, wherein tab 128-1 is configured to lock with tab 129-1 and tab 128-2 is configured to lock with tab 129-2. The interlocking mechanisms are for use in locking the arrays together in a predefined arrangement, which in this embodiment includes a cage shape. As a result of locking the two or more modular arrays together, the interlocking mechanisms ensure the ability to perform a registration of a location of the array of reference sensors 110 with respect to a positioning of the electromagnetic field generator 12.

Figure 8:
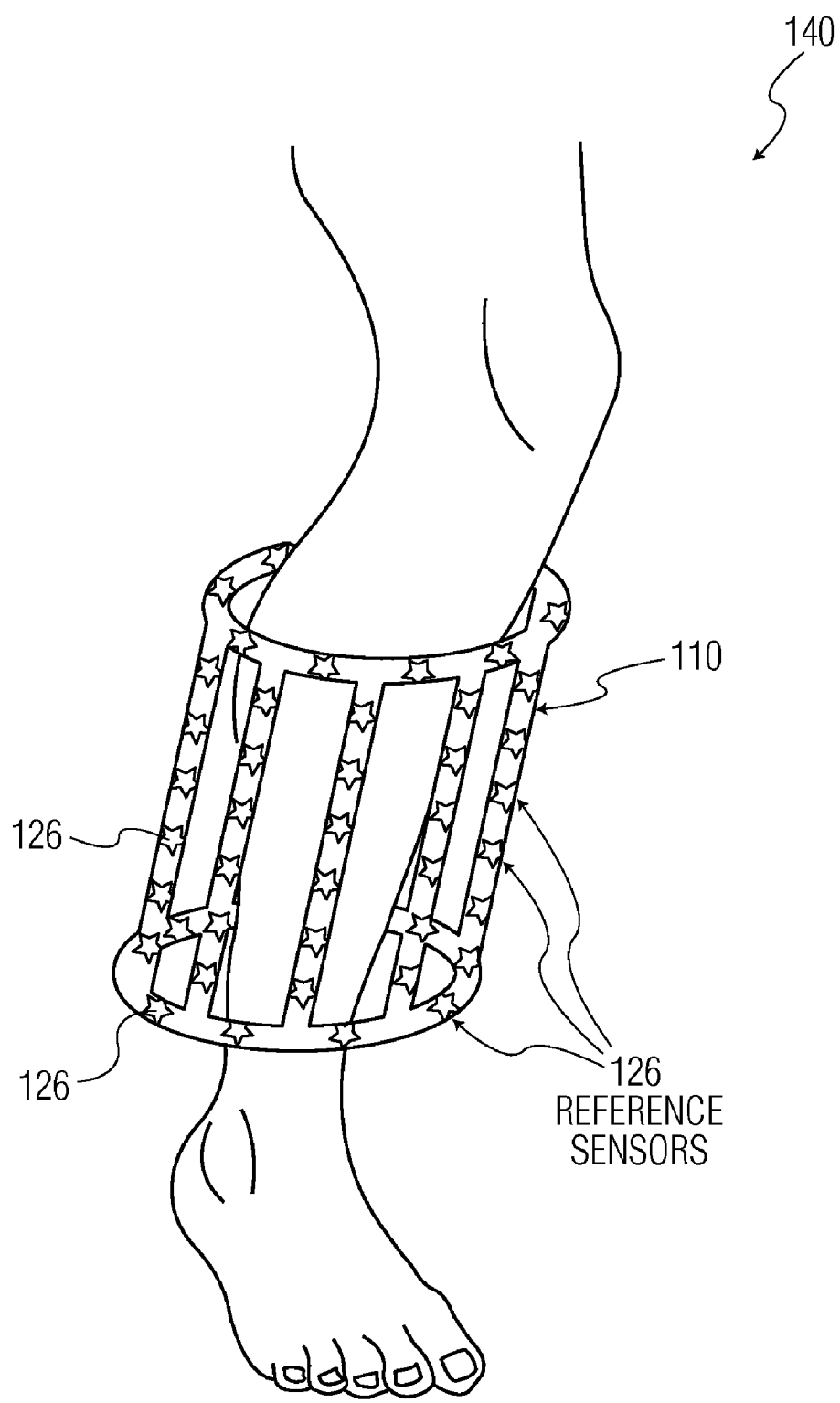
FIG. 8 is a schematic diagram view illustrating the array of reference sensors of FIG. 7 for use in an application according to one embodiment of the present disclosure.

FIG. 8 is a schematic diagram view illustrating the array of reference sensors of FIG. 7 for use in an application according to one embodiment of the present disclosure. In other words, the modular array 110 comprises an array having a cage shape, the cage array being configured for interventions in a peripheral limb 140 of a patient. The array of reference sensors 110 can thus be characterized by a given overall number of reference sensors in a given overall configuration. Accordingly, with knowledge of the positioning of at least one or more of the sensors within the overall configuration, the position and location information for a remainder of the sensors can be determined as a function of predetermined configuration information of the array of reference sensors. That is, the one or more sensors are configured for providing a description of the three dimensional (3D) orientation and position of the modular array of reference sensors.

According to another embodiment of the present disclosure, an electromagnetic tracking method featuring compensation of metal artifacts is disclosed. The method includes providing an electromagnetic field generator for generating an electromagnetic field in a region of interest. It is noted that the electromagnetic field is subject to distortion in response to a presence of metal artifacts proximate the electromagnetic field and the region of interest. The method further includes providing an array of reference sensors disposed proximate the region of interest, the array of reference sensors having a predefined known configuration. A first set of locations of the array of reference sensors is determined with respect to the electromagnetic field generator in response to an excitation of one or more of the reference sensors via the electromagnetic field. Using a second mechanism, other than the electromagnetic field, a first portion of a second set of locations of at least one or more reference sensors of the array of reference sensors is determined with respect to the second mechanism. The second mechanism is in a known spatial relationship with the electromagnetic field generator.

A remainder portion of the second set of locations of the reference sensors of the array of reference sensors is then determined in response to (i) the first portion of the second set of locations determined using the second mechanism and (ii) the predefined known configuration of the array of reference sensors. Subsequently, the method includes compensating for metal distortion of the electromagnetic field in the region of interest as a function of the first and second sets of reference sensor locations of the array of reference sensors. The method can further comprise determining a location of a sensor to be tracked within the region of interest as a function of the metal distortion compensated electromagnetic field.

In one embodiment, the second mechanism is further configured for determining the spatial relationship between the second mechanism and the electromagnetic field generator. The second mechanism can comprise, for example, an optical tracking system. In another embodiment, the second mechanism can comprise one or more of a suitable direct physical measurement, a suitable audio localization, or suitable radio localization according to the requirements of a particular electromagnetic tracking system application.

The array of reference sensors can comprise one or more modular arrays, each modular array having (i) a predefined configuration or shape and (ii) one or more reference sensors. In one embodiment, the modular array comprises an array having a semi-cylindrical shape, the semi-cylindrical shaped array being configured for use with interventions conducted around one or more of the abdomen or thorax of a patient. In another embodiment, the modular array comprises a substantially flat panel array, the flat panel array including one or more reference sensors in a predefined configuration, the flat panel array further being configured for placement underneath a patient. The flat panel array is intended for use on a table containing metal components, wherein the table can comprise one or more of an X-ray table or a CT table. In yet another embodiment, the modular array comprises an array having a cage shape, the cage array being configured for interventions in a head and/or a peripheral limb of a patient.

The modular array may further comprise modular portions of prefabricated sensor arrays, the modular portions further having at least two registration mechanisms, the registration mechanisms can comprise any suitable mechanism(s) for use in establishing a predefined placement of the modular portions together. The at least two registration mechanisms can comprise, for example, any suitable interlocking mechanisms. The interlocking mechanisms can be used for locking two or more modular arrays together in a predefined arrangement. Furthermore, the registration mechanisms provide for enabling an ability to perform a registration of a location of the array of reference sensors to a positioning of the electromagnetic field generator.

In another embodiment, the array of reference sensors can comprise first and second reference sensor arrays. The first reference sensor array includes a first configuration of one or more reference sensors. The second reference sensor array includes a second configuration of one or more reference sensors. In one embodiment, the first configuration differs from the second configuration.

In another embodiment, the array of reference sensors comprises a first array of reference sensors and a second array of reference sensors, wherein the second array of reference sensors is maintained physically separate from the first array of reference sensors. In another embodiment, the array of reference sensors is embedded within a non-metallic material of a desired shape. The desired shape can include one or more of (i) a semi-cylindrical shape, (ii) a substantially flat panel shape, or (iii) a cage shape.

The embodiments of the present disclosure include the use of prefabricated arrays of reference sensors. These arrays provide a simple, fast, and clinically practical method for monitoring a magnetic field for distortions in an EMTS system. Corrective transformations can then be calculated and applied during an intervention (for example, as disclosed in U.S. Pat. Nos. 6,400,139 and 6,377,041).

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure could be used to correct for distortions introduced by medical instruments, implants, imaging equipment, and/or a medical bed, table, or other mechanism supporting the patient. The embodiments could also be used for any number of image guided interventional medical procedures (biopsies, radio-frequency ablations, cryo-ablations, brachytherapy, catheterization, chemoembolization, etc.) targeted to various organs (liver, heart, brain, prostate, etc.). Furthermore, image guidance could be provided by any combination of ultrasound, MRI, CT, x-ray, PET, SPECT, and/or optical imaging. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. An electromagnetic tracking method featuring compensation of metal artifacts, comprising:
   providing an electromagnetic field generator (12) for generating an electromagnetic field (14) in a region of interest (16), wherein the electromagnetic field is subject to distortion in response to a presence of metal artifacts proximate the electromagnetic field and the region of interest;
   providing an array of reference sensors (30,50,102,104, 110) disposed proximate the region of interest, the array of reference sensors having a predefined known configuration;
   determining a first set of locations of the array of reference sensors with respect to the electromagnetic field generator in response to an excitation of one or more of the reference sensors via the electromagnetic field;
   using a second mechanism (28), other than the electromagnetic field, for determining a first portion of a second set of locations of at least one or more reference sensor of the array of reference sensors with respect to the second mechanism, the second mechanism being in a known spatial relationship with the electromagnetic field generator;
   determining a remainder portion of the second set of locations of the reference sensors of the array of reference sensors in response to (i) the first portion of the second set of locations determined using the second mechanism and (ii) the predefined known configuration of the array of reference sensors; and
   compensating for metal distortion of the electromagnetic field in the region of interest as a function of the first and second sets of reference sensor locations of the array of reference sensors.

2. The method of claim 1, wherein the second mechanism (28) is further configured for determining the spatial relationship between the second mechanism and the electromagnetic field generator.

3. The method of claim 2, wherein the second mechanism (28) comprises an optical tracking system.

4. The method of claim 2, wherein the second mechanism (28) comprises one or more of a direct physical measurement, an audio localization, or radio localization.

5. The method of claim 1, further comprising:
   determining a location of a sensor (20) to be tracked within the region of interest as a function of the metal distortion compensated electromagnetic field.

6. The method of claim 1, wherein the array of reference sensors (30,50,102,104,110) comprises one or more modular arrays, each modular array having (i) a predefined configuration or shape and (ii) one or more reference sensors.

7. The method of claim 6, wherein the modular array (60) further comprises modular portions of prefabricated sensor arrays, the modular portions further having at least two registration mechanisms (48,49,128,129), the registration mechanisms for use in establishing a predefined placement of the modular portions together.

8. The method of claim 7, further wherein the at least two registration mechanisms comprise interlocking mechanisms, the interlocking mechanisms for use in locking two or more modular arrays together in a predefined arrangement, and further for enabling an ability to perform a registration of a location of the array of reference sensors to a positioning of the electromagnetic field generator.

9. The method of claim 1, wherein the array of reference sensors comprise first and second reference sensor arrays, the first reference sensor array having a first configuration of one or more reference sensors and the second reference sensor array having a second configuration of one or more reference sensors, the first configuration being different from the second configuration.

10. The method of claim 1, wherein the array of reference sensors comprises a first array of reference sensors (102), the method further comprising:
using a second array of reference sensors (104), the second array of reference sensors being maintained physically separate from the first array of reference sensors.

11. The method of claim 1, wherein the array of reference sensors is embedded within a non-metallic material of a desired shape.

12. The method of claim 11, wherein the desired shape includes one or more of (i) a semi-cylindrical shape, (ii) a substantially flat panel shape, or (iii) a cage shape.

13. An electromagnetic tracking system (10) featuring compensation of metal artifacts, comprising:
an electromagnetic field generator (12) for generating an electromagnetic field (14) in a region of interest (16), wherein the electromagnetic field is subject to distortion in response to a presence of metal artifacts proximate the electromagnetic field and the region of interest;
at least one array of reference sensors (30,50,102,104,110) disposed proximate the region of interest, the at least one array of reference sensors having a predefined known configuration;
a system controller (18) for determining a first set of locations of the array of reference sensors with respect to the electromagnetic field generator in response to an excitation of one or more of the reference sensors via the electromagnetic field; and
a second mechanism (28), other than the electromagnetic field generator, for determining a first portion of a second set of locations of at least one or more reference sensor of the array of reference sensors with respect to the second mechanism, the second mechanism being in a known spatial relationship with the electromagnetic field generator,
wherein the system controller is further for determining a remainder portion of the second set of locations of the reference sensors of the array of reference sensors in response to (i) the first portion of the second set of locations determined using the second mechanism and (ii) the predefined known configuration of the array of reference sensors, and for compensating for metal distortion of the electromagnetic field in the region of interest as a function of the first and second sets of reference sensor locations of the array of reference sensors.

14. The system of claim 13, wherein the second mechanism (28) is further configured for determining the spatial relationship between the second mechanism and the electromagnetic field generator.

15. The system of claim 14, wherein the second mechanism (28) comprises an optical tracking system.

16. The system of claim 13, further wherein the system controller (18) is further for determining a location of a sensor (20) to be tracked within the region of interest as a function of the metal distortion compensated electromagnetic field.

17. The system of claim 13, wherein the array of reference sensors (30,50,102,104,110) comprises one or more modular arrays, each modular array having (i) a predefined configuration or shape and (ii) one or more reference sensors.

18. The system of claim 17, wherein the modular array (30,102,104) comprises an array having a semi-cylindrical shape, the semi-cylindrical shaped array being configured for use with interventions conducted around one or more of the abdomen or thorax of a patient.

19. The system of claim 17, wherein the modular array (50) comprise a substantially flat panel array, the flat panel array including one or more reference sensors in a predefined configuration, the flat panel array further being configured for placement underneath a patient.

20. The system of claim 17, wherein the modular array (110) comprises an array having a cage shape, the cage array being configured for interventions in a peripheral limb of a patient.

21. The system of claim 17, wherein the modular array (60) further comprises one or more modular portions of prefabricated sensor arrays, the modular portions further having at least two registration mechanisms (48,49,128,129), the registration mechanisms for use in establishing a predefined placement of the modular portions together.

22. The system of claim 21, further wherein the at least two registration mechanisms comprise interlocking mechanisms, the interlocking mechanisms for use in locking two or more modular arrays together in a predefined arrangement, and further for enabling an ability to perform a registration of a location of the array of reference sensors to a positioning of the electromagnetic field generator.

23. The system of claim 13, wherein the array of reference sensors comprise first and second reference sensor arrays, the first reference sensor array having a first configuration of one or more reference sensors and the second reference sensor array having a second configuration of one or more reference sensors, the first configuration being different from the second configuration.

24. The system of claim 13, wherein the array of reference sensors comprises a first array of reference sensors (102), the system further comprising:
a second array of reference sensors (104), the second array of reference sensors being maintained physically separate from the first array of reference sensors.

25. The system of claim 13, wherein the array of reference sensors is embedded within a non-metallic material of a desired shape.

26. The system of claim 25, wherein the desired shape includes one or more of (i) a semi-cylindrical shape, (ii) a substantially flat panel shape, or (iii) a cage shape.

* * * * *